United States Patent
Aller et al.

(10) Patent No.: US 12,239,164 B2
(45) Date of Patent: *Mar. 4, 2025

(54) AEROSOL DELIVERY DEVICE WITH VISIBLE INDICATOR

(71) Applicant: RAI Strategic Holdings, Inc., Winston-Salem, NC (US)

(72) Inventors: Jared Aller, Winston-Salem, NC (US); Charles Jacob Novak, III, Winston-Salem, NC (US); Sean A. Daugherty, Yadkinville, NC (US); Michael Ryan Galloway, Winston-Salem, NC (US); Matthew Joel Nettenstrom, Bartlett, IL (US); Thomas Michael McKeon, Wheaton, IL (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/618,302

(22) Filed: Mar. 27, 2024

(65) Prior Publication Data

US 2024/0237731 A1 Jul. 18, 2024

Related U.S. Application Data

(63) Continuation of application No. 18/312,912, filed on May 5, 2023, now Pat. No. 11,974,603, which is a (Continued)

(51) Int. Cl.
*A24F 40/42* (2020.01)
*A24B 15/167* (2020.01)
(Continued)

(52) U.S. Cl.
CPC ............ *A24F 40/42* (2020.01); *A24B 15/167* (2016.11); *A24D 1/002* (2013.01); *A24D 1/14* (2013.01);
(Continued)

(58) Field of Classification Search
None
See application file for complete search history.

(56) References Cited

U.S. PATENT DOCUMENTS 2,057,353 A 10/1936 Whittemore, Jr.
2,104,266 A 1/1938 McCormick
(Continued)

FOREIGN PATENT DOCUMENTS

CL 2012003241 9/2013
CL 2017001137 1/2018
(Continued)

OTHER PUBLICATIONS

International Search Report from corresponding International Appl. No. PCT/IB2019/058620, mailed Jan. 3, 2020.

*Primary Examiner* — Tho D Ta
(74) *Attorney, Agent, or Firm* — Womble Bond Dickinson (US) LLP

(57) ABSTRACT

The present disclosure relates to aerosol delivery devices and cartridges for aerosol delivery devices. The cartridge comprises a mouthpiece having a proximal end and a distal end, the proximal end of the mouthpiece having an exit portal defined therethrough, a tank defining a proximal end and a closed distal end, the tank being configured to contain a liquid composition that includes a distinctive characteristic, and a heater configured to heat the liquid composition. The distal end of the mouthpiece is configured to engage the proximal end of the tank, and when the cartridge is coupled with the aerosol delivery device at least one feature of the (Continued)

cartridge, or at least one feature of the control device, or at least one feature of both the cartridge and the control device, provides a visual indication of a color associated with the distinctive characteristic.

15 Claims, 7 Drawing Sheets

Related U.S. Application Data continuation of application No. 17/683,988, filed on Mar. 1, 2022, now Pat. No. 11,678,700, which is a continuation of application No. 16/171,920, filed on Oct. 26, 2018, now Pat. No. 11,291,249.

(60) Provisional application No. 62/744,978, filed on Oct. 12, 2018.

(51) Int. Cl.
  *A24D 1/00* (2020.01)
  *A24D 1/14* (2006.01)
  *A24F 7/00* (2006.01)
  *A24F 7/02* (2006.01)
  *A24F 40/46* (2020.01)
  *A61M 11/04* (2006.01)
  *H01R 13/17* (2006.01)
  *H01R 13/62* (2006.01)
  *H05B 3/20* (2006.01)
  *A24F 40/40* (2020.01)

(52) U.S. Cl.
  CPC .............. *A24F 7/00* (2013.01); *A24F 7/02* (2013.01); *A24F 40/46* (2020.01); *A61M 11/042* (2014.02); *H01R 13/17* (2013.01); *H01R 13/6205* (2013.01); *H05B 3/20* (2013.01); *A24F 40/40* (2020.01); *A61M 11/041* (2013.01); *A61M 2205/0288* (2013.01); *A61M 2205/3368* (2013.01); *A61M 2205/50* (2013.01); *A61M 2205/584* (2013.01); *A61M 2205/587* (2013.01); *A61M 2205/8206* (2013.01); *H05B 2203/021* (2013.01)

(56) References Cited

U.S. PATENT DOCUMENTS

| | | |
|---|---|---|
| 3,200,819 A | 8/1965 | Gilbert |
| 4,922,901 A | 5/1990 | Brooks et al. |
| 5,060,671 A | 10/1991 | Counts et al. |
| 5,093,894 A | 3/1992 | Deevi et al. |
| 5,894,841 A | 4/1999 | Voges |
| 6,125,853 A | 10/2000 | Susa et al. |
| 6,155,268 A | 12/2000 | Takeuchi |
| 7,117,867 B2 | 10/2006 | Cox et al. |
| 7,832,410 B2 | 11/2010 | Hon |
| 8,314,591 B2 | 11/2012 | Terry et al. |
| 8,365,742 B2 | 2/2013 | Hon |
| 8,499,766 B1 | 8/2013 | Newton |
| 8,528,569 B1 | 9/2013 | Newton |
| 8,833,364 B2 | 9/2014 | Buchberger |
| 8,950,395 B2 | 2/2015 | Schennum |
| 9,220,304 B2 | 12/2015 | Greim |
| 9,451,791 B2 | 9/2016 | Sears et al. |
| 9,462,831 B2 | 10/2016 | Liu |
| 9,877,508 B2 | 1/2018 | Kane |
| 10,015,990 B2 | 7/2018 | Mironov |
| 10,028,537 B1 | 7/2018 | Hawes et al. |
| 10,058,125 B2 | 8/2018 | Worm et al. |
| 10,080,851 B2 | 9/2018 | Davidson et al. |
| 10,085,481 B2 | 10/2018 | Verleur et al. |
| 10,092,037 B2 | 10/2018 | Tucker et al. |
| 10,104,913 B2 | 10/2018 | Lau et al. |
| 10,117,463 B2 | 11/2018 | Thomas, Jr. |
| 10,117,467 B2 | 11/2018 | Hawes et al. |
| 10,791,767 B2 | 10/2020 | Novak, III et al. |
| 11,185,110 B2 | 11/2021 | Fraser et al. |
| 11,291,249 B2 * | 4/2022 | Aller .................... H05B 1/0244 |
| 11,678,700 B2 | 6/2023 | Aller et al. |
| 2005/0016550 A1 | 1/2005 | Katase |
| 2006/0196518 A1 | 9/2006 | Hon |
| 2008/0092912 A1 | 4/2008 | Robinson et al. |
| 2009/0095311 A1 | 4/2009 | Han |
| 2009/0126745 A1 | 5/2009 | Hon |
| 2009/0151717 A1 | 6/2009 | Bowen et al. |
| 2009/0188490 A1 | 7/2009 | Han |
| 2009/0272379 A1 | 11/2009 | Thorens et al. |
| 2009/0320863 A1 | 12/2009 | Fernando et al. |
| 2011/0094523 A1 | 4/2011 | Thorens et al. |
| 2011/0126848 A1 | 6/2011 | Zuber et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2013/0037041 A1 | 2/2013 | Worm et al. |
| 2013/0042865 A1 | 2/2013 | Monsees et al. |
| 2013/0306084 A1 | 11/2013 | Flick |
| 2013/0319435 A1 | 12/2013 | Flick |
| 2014/0000638 A1 | 1/2014 | Sebastian et al. |
| 2014/0096781 A1 | 4/2014 | Sears et al. |
| 2014/0096782 A1 | 4/2014 | Ampolini et al. |
| 2014/0253144 A1 | 9/2014 | Novak, III et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0366898 A1 | 12/2014 | Monsees et al. |
| 2015/0020832 A1 | 1/2015 | Greim et al. |
| 2015/0128976 A1 | 5/2015 | Verleur et al. |
| 2015/0150308 A1 | 6/2015 | Monsees et al. |
| 2015/0164142 A1 | 6/2015 | Li et al. |
| 2015/0208729 A1 | 7/2015 | Monsees et al. |
| 2015/0216233 A1 | 8/2015 | Sears et al. |
| 2015/0305406 A1 | 10/2015 | Li et al. |
| 2015/0313287 A1 | 11/2015 | Verleur et al. |
| 2015/0328415 A1 | 11/2015 | Minskoff et al. |
| 2016/0235121 A1 | 8/2016 | Rogan et al. |
| 2016/0278436 A1 | 9/2016 | Verleur et al. |
| 2016/0345630 A1 | 12/2016 | Mironov et al. |
| 2016/0366947 A1 | 12/2016 | Monsees et al. |
| 2017/0027226 A1 | 2/2017 | Mironov et al. |
| 2017/0071256 A1 | 3/2017 | Verleur et al. |
| 2017/0095005 A1 | 4/2017 | Monsees et al. |
| 2017/0135404 A1 | 5/2017 | Reevell |
| 2017/0135405 A1 | 5/2017 | Reevell |
| 2017/0143042 A1 | 5/2017 | Batista et al. |
| 2017/0215485 A1 | 8/2017 | Zitzke |
| 2017/0231281 A1 | 8/2017 | Hatton et al. |
| 2017/0231282 A1 | 8/2017 | Bowen et al. |
| 2017/0325289 A1 | 11/2017 | Liu |
| 2017/0340011 A1 | 11/2017 | Batista |
| 2017/0340012 A1 | 11/2017 | Mironov et al. |
| 2017/0347711 A1 | 12/2017 | Litten et al. |
| 2017/0347712 A1 | 12/2017 | Singh |
| 2017/0367402 A1 | 12/2017 | Lau et al. |
| 2018/0000157 A1 | 1/2018 | Batista et al. |
| 2018/0000160 A1 | 1/2018 | Taschner et al. |
| 2018/0014575 A1 | 1/2018 | Fursa |
| 2018/0020726 A1 | 1/2018 | Alarcon et al. |
| 2018/0020731 A1 | 1/2018 | Rasmussen et al. |
| 2018/0020736 A1 | 1/2018 | Silvestrini |
| 2018/0035717 A1 | 2/2018 | Batista |
| 2018/0042306 A1 | 2/2018 | Atkins et al. |
| 2018/0043114 A1 | 2/2018 | Bowen et al. |
| 2018/0077967 A1 | 3/2018 | Hatton et al. |
| 2018/0084828 A1 | 3/2018 | Phillips et al. |
| 2018/0084831 A1 | 3/2018 | Mironov |
| 2018/0103685 A1 | 4/2018 | Yener |
| 2018/0132525 A1 | 5/2018 | Patil et al. |
| 2018/0140019 A1 | 5/2018 | Guo et al. |
| 2018/0153220 A1 | 6/2018 | Verleur et al. |
| 2018/0168227 A1 | 6/2018 | Fraser et al. |
| 2018/0177230 A1 | 6/2018 | Hawes et al. |

(56) References Cited

U.S. PATENT DOCUMENTS

| | | | |
|---|---|---|---|
| 2018/0213850 A1 | 8/2018 | Brinkley et al. |
| 2018/0228214 A1 | 8/2018 | McAdam et al. |
| 2018/0242643 A1 | 8/2018 | Silvestrini et al. |
| 2018/0280637 A1 | 10/2018 | Mayle et al. |
| 2018/0295888 A1 | 10/2018 | Newcomb et al. |
| 2018/0296777 A1 | 10/2018 | Terry et al. |
| 2019/0289909 A1 | 9/2019 | Hejazi |
| 2019/0373679 A1 | 12/2019 | Fu et al. |
| 2020/0113244 A1 | 4/2020 | Novak, III et al. |

FOREIGN PATENT DOCUMENTS

| | | |
|---|---|---|
| CL | 2017003454 | 6/2018 |
| CL | 2021000899 | 9/2021 |
| CL | 2021000900 | 9/2021 |
| CN | 1541577 | 11/2004 |
| CN | 2719043 | 8/2005 |
| CN | 201379072 | 1/2010 |
| CN | 106263031 | 1/2017 |
| CN | 107890142 | 4/2018 |
| EP | 1 618 803 | 1/2006 |
| EP | 2 779 851 | 10/2016 |
| TW | 201825827 | 7/2018 |
| WO | WO 2004/080216 | 9/2004 |
| WO | WO 2005/099494 | 10/2005 |
| WO | WO 2007/131449 | 11/2007 |
| WO | WO 2015/071703 | 5/2015 |
| WO | WO 2016/005533 | 1/2016 |
| WO | WO 2016/026811 | 2/2016 |
| WO | WO 2016/154797 | 10/2016 |
| WO | WO 2017/051006 | 3/2017 |
| WO | WO 2017/055803 | 4/2017 |
| WO | WO 2017/102969 | 6/2017 |
| WO | WO 2017/163046 | 9/2017 |
| WO | WO 2017/207442 | 12/2017 |
| WO | WO 2018/167166 | 9/2018 |
| WO | WO 2018/202732 | 11/2018 |
| WO | WO 2018/206940 | 11/2018 |
| WO | WO 2020/075139 | 4/2020 |

* cited by examiner

AEROSOL DELIVERY DEVICE WITH VISIBLE INDICATOR

CROSS-REFERENCE TO RELATED APPLICATIONS

This application is a continuation of U.S. patent application Ser. No. 18/312,912, titled Aerosol Delivery Device With Visible Indicator, filed on May 5, 2023, which is a continuation of U.S. patent application Ser. No. 17/683,988, titled Aerosol Delivery Device with Visible Indicator, filed on Mar. 1, 2022, which is a continuation of U.S. patent application Ser. No. 16/171,920, titled Aerosol Delivery Device with Visible Indicator, filed on Oct. 26, 2018, which claims priority to, and the benefit of, U.S. Provisional Patent Application No. 62/744,978, titled Aerosol Forming Device, filed on Oct. 12, 2018, each of which is incorporated herein in its entirety by reference.

FIELD OF THE DISCLOSURE

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. Pat. Pub. No. 2014/0096781 to Sears et al., which are incorporated herein by reference in their entireties. See also, for example, the various types of smoking articles, aerosol delivery devices, and electrically powered heat generating sources referenced by brand name and commercial source in U.S. patent application Ser. No. 14/170,838 to Bless et al., filed Feb. 3, 2014, which is incorporated herein by reference in its entirety.

It would be desirable to provide an aerosol delivery device with advantageous usability features. In particular, it would be desirable to provide an aerosol delivery device and a cartridge for use in an aerosol delivery device that provide visual indication of one or more characteristics of the device.

SUMMARY OF THE DISCLOSURE

The present disclosure relates to aerosol delivery devices, methods of forming such devices, and elements of such devices. The disclosure particularly can relate to an aerosol delivery device and a cartridge for removable use with an aerosol delivery device.

In various implementations, the present disclosure provides an aerosol delivery device. In one implementation, the aerosol delivery device may comprise a control device that includes an outer housing defining an outer wall and having a proximal end and a distal end, the proximal end of the control device defining a cartridge receiving chamber, the control device further including a battery and a control component, and a cartridge that includes a mouthpiece and a tank, the mouthpiece having a proximal end and a distal end, the proximal end of the mouthpiece having an exit portal defined therethrough and the distal end of the mouthpiece configured to engage a proximal end of the tank, the tank further defining a closed distal end and being configured to contain a liquid composition that includes a distinctive characteristic, the cartridge further including a heater configured to heat the liquid composition. The cartridge may be configured to be removably coupled with the cartridge receiving chamber of the control device, and when the cartridge is coupled with the control device at least one feature of the cartridge, or at least one feature of the control device, or at least one feature of both the cartridge and the control device, may provide a visual indication of a color associated with the distinctive characteristic. In some implementations, the distinctive characteristic may comprise a flavorant included in the liquid composition. In some implementations, the distinctive characteristic may comprise a nicotine strength of the liquid composition. In some implementations, the control device may define at least a portion of an indication window, the distal end of tank may include an indicator band comprising the color associated with the distinctive characteristic, and at least a portion of the indicator band may be visible through the indication window. In some implementations, the control device may define the indication window. In some implementations, the control device and the cartridge each may define a portion of the indication window. In some implementations, the indicator band may include a projection that extends from the indicator band, and the projection may be visible through the indication window. In some implementations, the projection may have a semi-circular shape. In some implementations, the control device may define at least a portion of an indication window, the tank may define a tank wall comprising the color associated with the distinctive characteristic, and at least a portion of the tank wall may be visible through the indication window. In some implementations, the tank wall may be one or more of at least partially transparent or at least partially translucent. In some implementations, the control device may define at least a portion of an indication window, the tank may define a tank wall that is one or more of at least partially transparent or at least partially translucent and the distal end of tank may include an indicator band comprising the color associated with the distinctive characteristic, at least a portion of the tank wall may be visible through the indication window, and at least a portion of the indicator band may also be visible through the indication window. In some implementations, the mouthpiece may define a flange positioned between the proximal end and the distal end thereof, the flange may be visible when the cartridge is coupled with the control device, and at least a portion of the flange may comprise the color associated with the distinctive characteristic.

In some implementations, the cartridge may include at least one light source, and the light source of the cartridge may comprise the color associated with the distinctive characteristic. In some implementations, the control device may include at least one light source configured to display a plurality of colors, and one of the colors may comprise the color associated with the distinctive characteristic. In some implementations, the cartridge may include a light source, the tank of the cartridge may define a tank wall comprising the color associated with the distinctive characteristic, the tank wall may be one or more of at least partially transparent or at least partially translucent, and light from the light source of the cartridge may be configured to pass through the tank wall of the cartridge. In some implementations, the control device may include a light source, the tank of the cartridge may define a tank wall comprising the color associated with the distinctive characteristic, the tank wall may be one or more of at least partially transparent or at least partially translucent, and light from the light source of the control device may be configured to pass through the tank wall of the cartridge. In some implementations, the control device may further include a light guide configured to facilitate illumination through the tank wall. In some implementations, the visual indication of the color associated with the distinctive characteristic may be triggered by any one or any combination of the following: a detection of the presence of the cartridge in the control body, a detection of a type of cartridge in the control body, a detection of a puff, a user initiated request. In some implementations, the mouthpiece may be defined by an outer mouthpiece wall, and the outer mouthpiece wall may provide the visual indication of a color associated with the distinctive characteristic. In some implementations, the exit portal of the mouthpiece may provide the visual indication of a color associated with the distinctive characteristic.

In various implementations, the present disclosure also provides a cartridge for removable use with an aerosol delivery device. In one implementation, the cartridge may comprise a mouthpiece having a proximal end and a distal end, the proximal end of the mouthpiece having an exit portal defined therethrough, a tank defining a proximal end and a closed distal end, the tank being configured to contain a liquid composition that includes a distinctive characteristic, and a heater configured to heat the liquid composition. The distal end of the mouthpiece may be configured to engage the proximal end of the tank, and when the cartridge is coupled with the aerosol delivery device, at least one feature of the cartridge may provide a visual indication of a color associated with the distinctive characteristic. In some implementations, the distinctive characteristic may comprise a flavorant included in the liquid composition. In some implementations, the distinctive characteristic may comprise a nicotine strength of the liquid composition. In some implementations, the distal end of the tank may include an indicator band comprising the color associated with the distinctive characteristic. In some implementations, the indicator band may include a projection that extends from the indicator band. In some implementations, the projection may have a semi-circular shape.

In some implementations, the tank may define a tank wall comprising the color associated with the distinctive characteristic. In some implementations, the tank wall may be one or more of at least partially transparent or at least partially translucent. In some implementations, the tank may define a tank wall that is one or more of at least partially transparent or at least partially translucent, and the distal end of tank may include an indicator band comprising the color associated with the distinctive characteristic. In some implementations, the mouthpiece may define a flange positioned between the proximal end and the distal end thereof, the flange may be visible when the cartridge is coupled with the control device, and at least a portion of the flange may comprise the color associated with the distinctive characteristic. In some implementations, the cartridge may include at least one light source, and the light source of the cartridge may comprise the color associated with the distinctive characteristic. In some implementations, the cartridge may include a light source, the tank of the cartridge may define a tank wall comprising the color associated with the distinctive characteristic, the tank wall may be one or more of at least partially transparent or at least partially translucent, and light from the light source of the cartridge may be configured to pass through the tank wall of the cartridge. In some implementations, the mouthpiece may be defined by an outer mouthpiece wall, and the outer mouthpiece wall may provide the visual indication of a color associated with the distinctive characteristic. In some implementations, the exit portal of the mouthpiece may provide the visual indication of a color associated with the distinctive characteristic.

These and other features, aspects, and advantages of the disclosure will be apparent from a reading of the following detailed description together with the accompanying drawings, which are briefly described below.

BRIEF DESCRIPTION OF THE FIGURES

Figure 1:
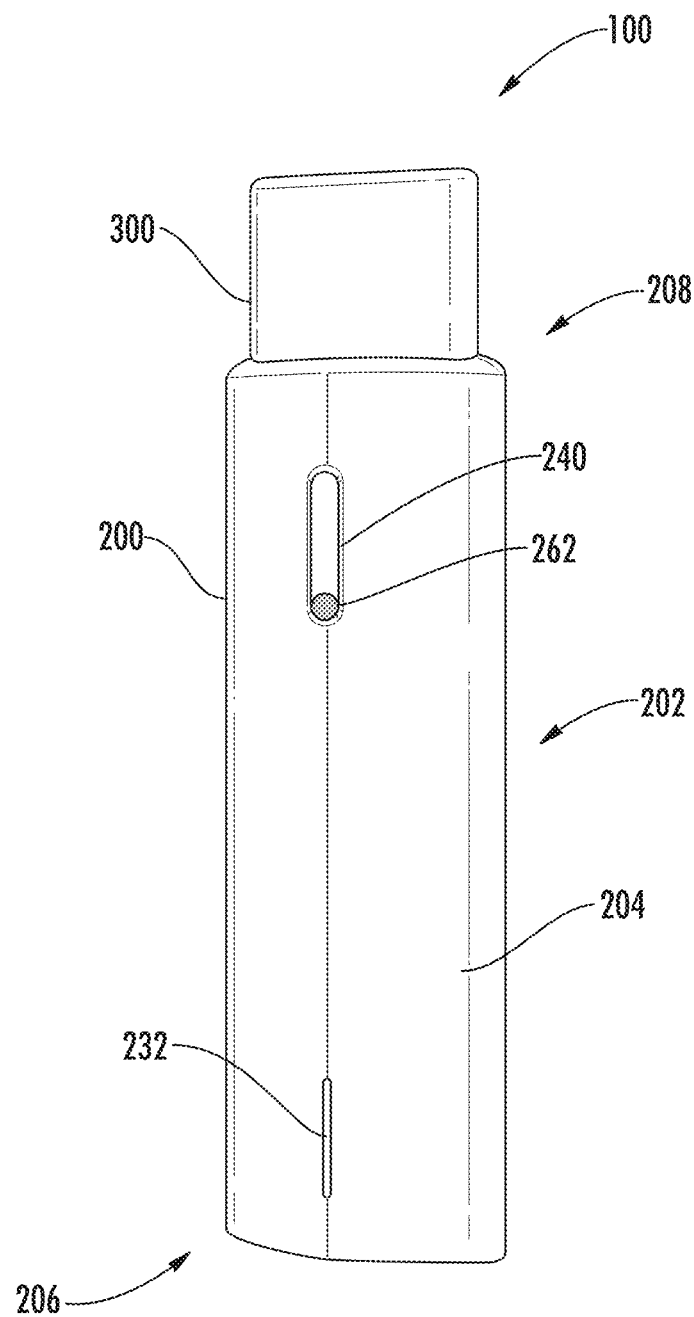
Figure 2:
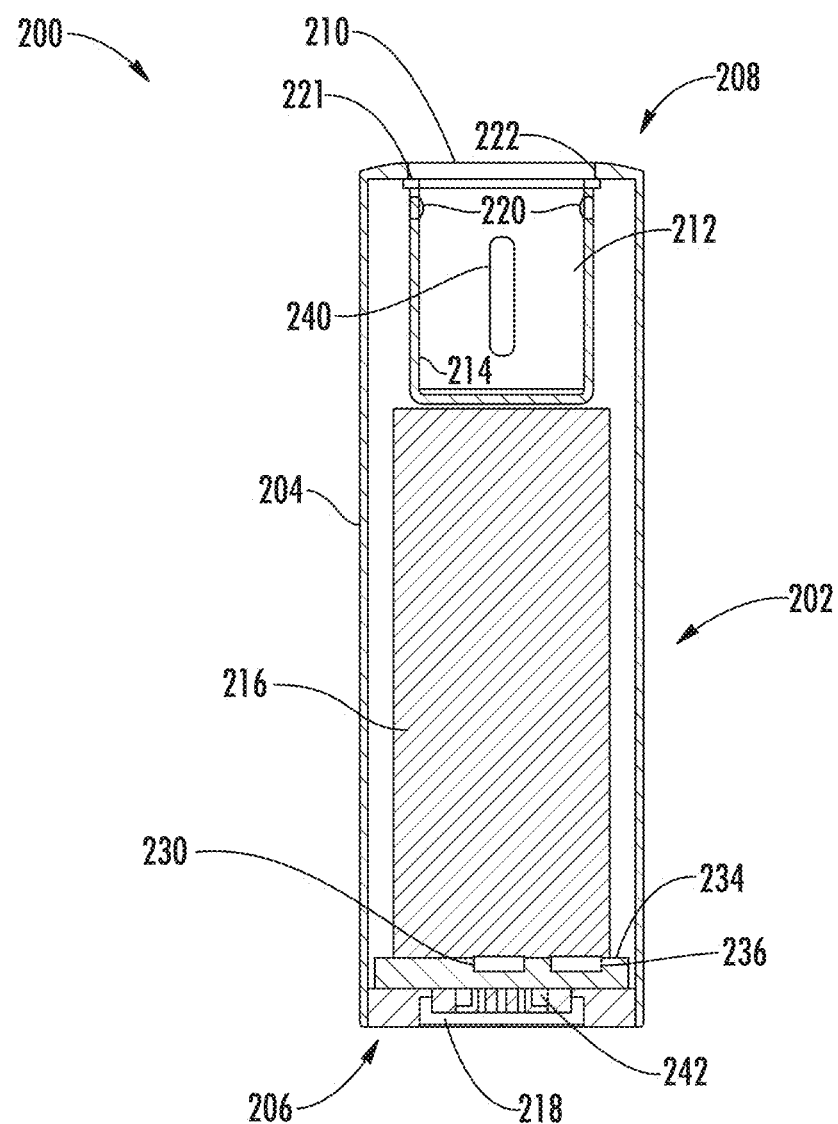
Figure 3:
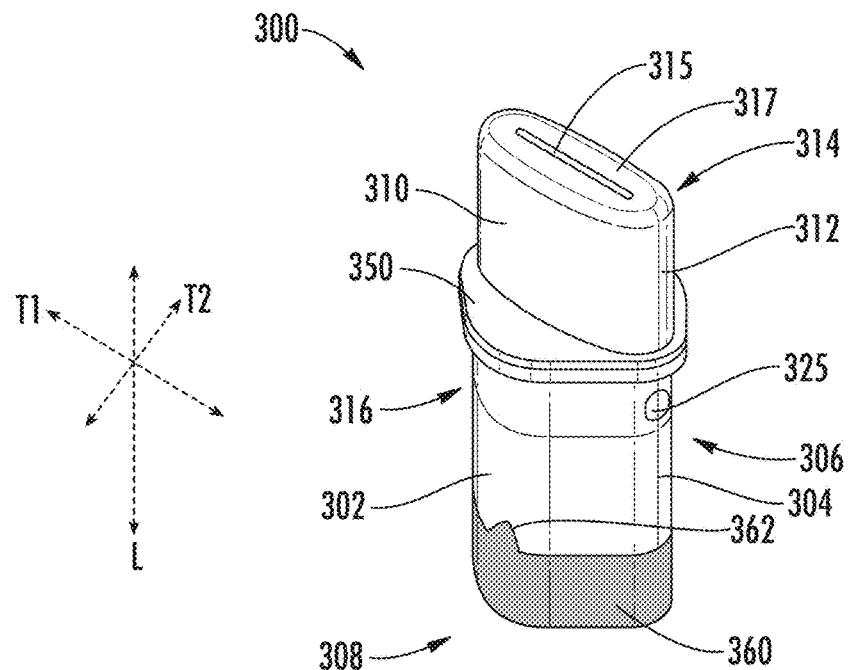
Figure 4:
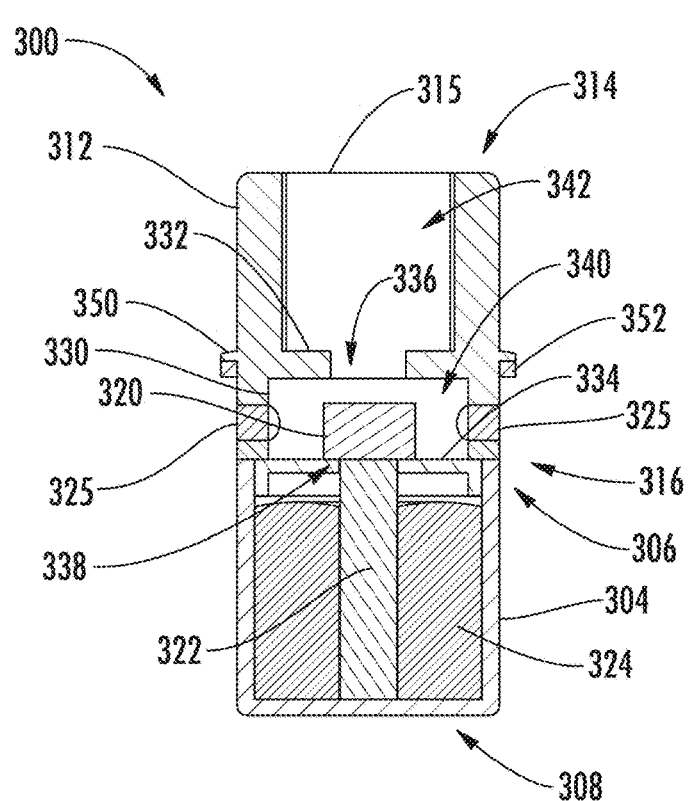
Figure 5:
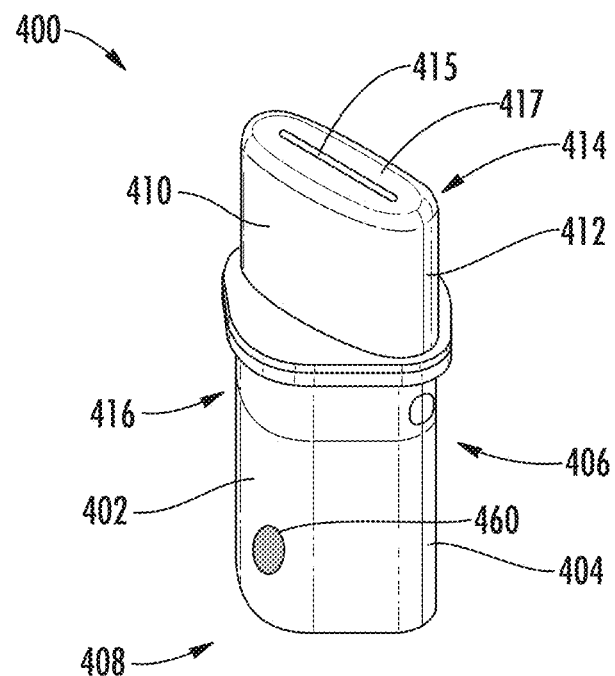
Figure 6:
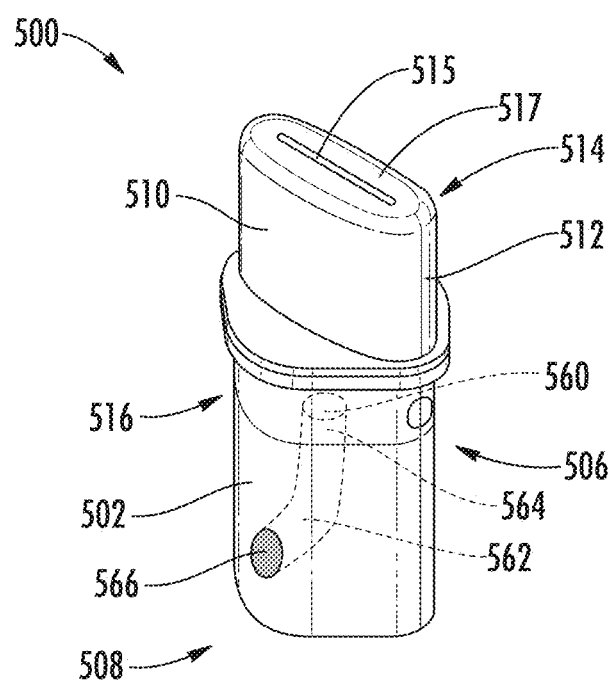
Figure 7:
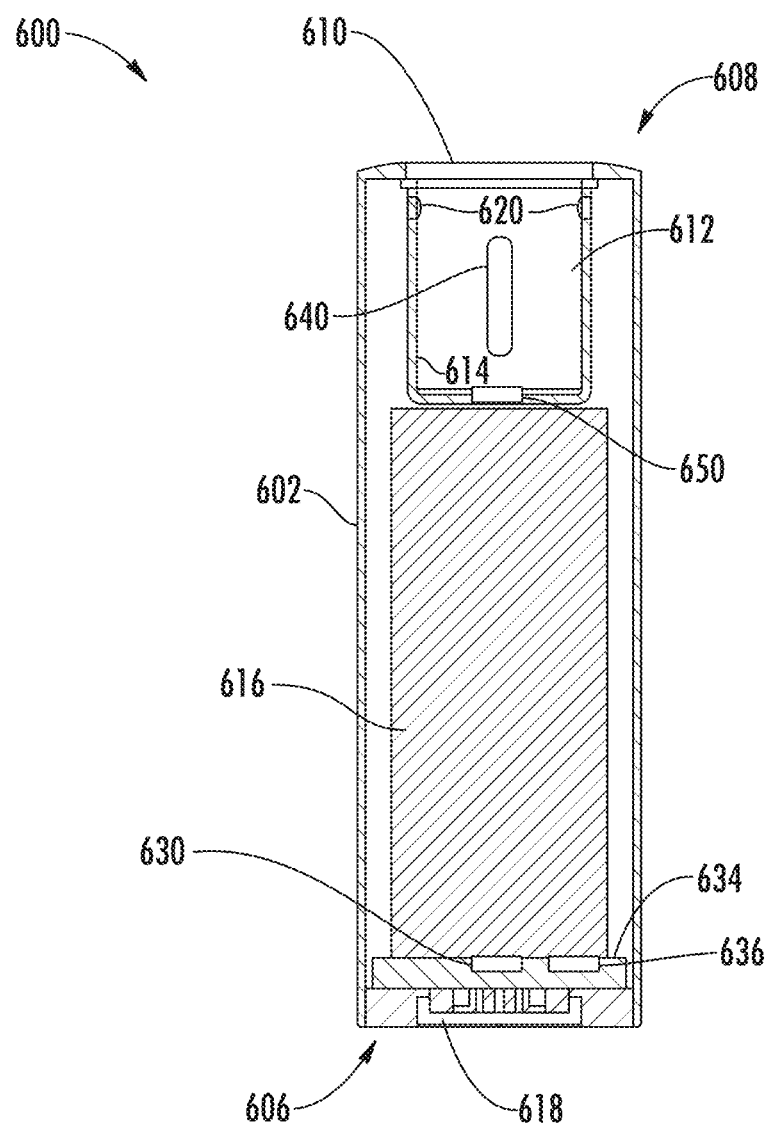
Figure 8:
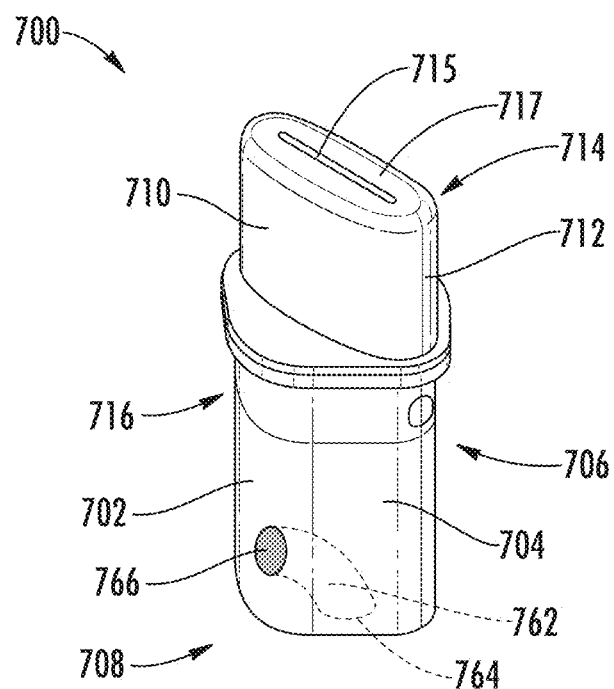
Figure 9:
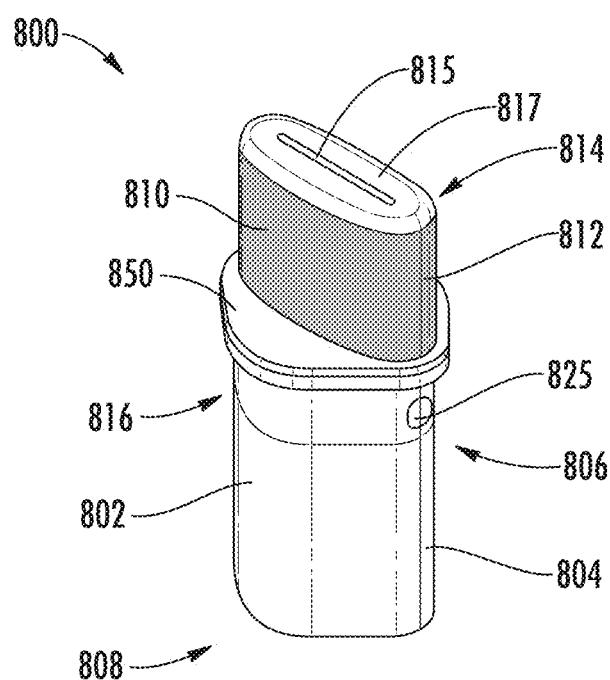
Figure 10:
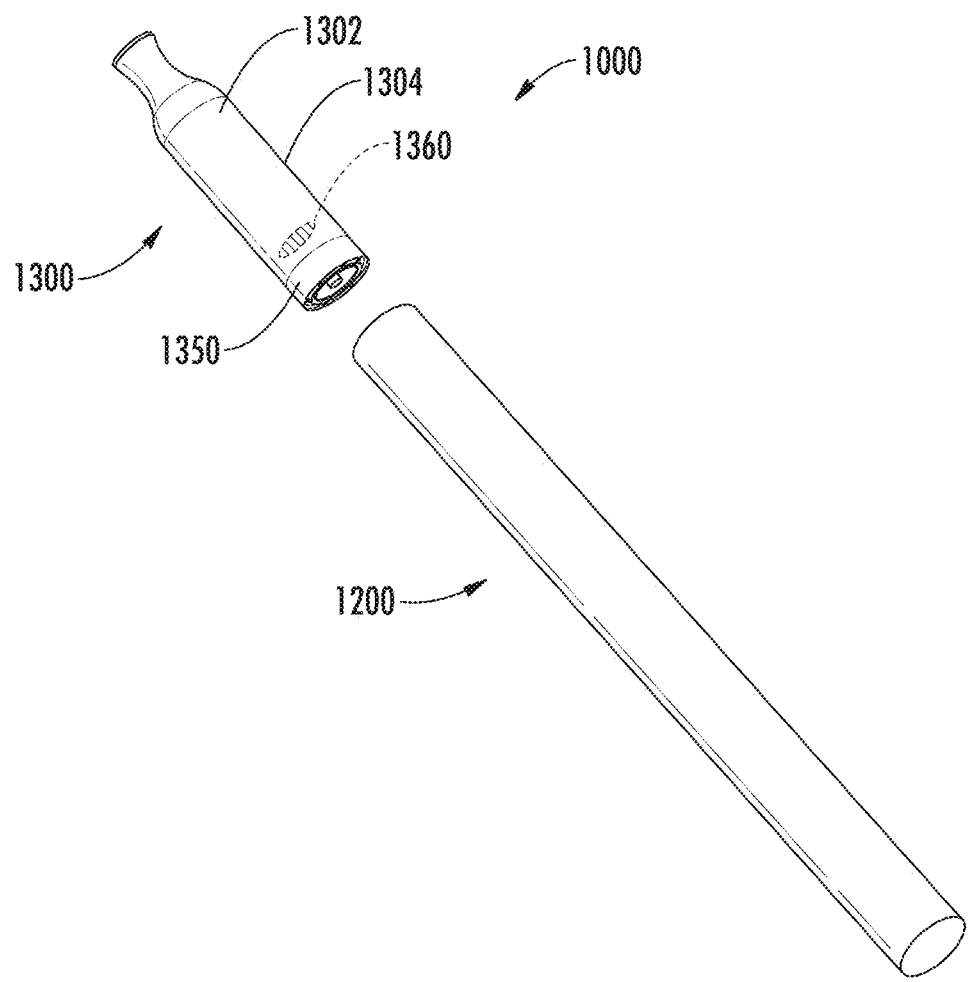

Having thus described the disclosure in the foregoing general terms, reference will now be made to the accompanying drawings, which are not necessarily drawn to scale, and wherein:

FIG. 1 illustrates a perspective view of an aerosol delivery device according to example implementations of the present disclosure;

FIG. 2 illustrates partial cross-section view of the control device of the aerosol delivery device illustrated in FIG. 1;

FIG. 3 illustrates a perspective view of a cartridge according to an example implementation of the present disclosure;

FIG. 4 illustrates a partial cross-section view of the cartridge illustrated in FIG. 3;

FIG. 5 illustrates a perspective view of a cartridge according to another example implementation of the present disclosure;

FIG. 6 illustrates a perspective view of a cartridge according to another example implementation of the present disclosure;

FIG. 7 illustrates partial cross-section view of a control device of an aerosol delivery device according to another implementation of the present disclosure;

FIG. 8 illustrates a perspective view of a cartridge according to another example implementation of the present disclosure;

FIG. 9 illustrates a perspective view of a cartridge according to another example implementation of the present disclosure; and FIG. 10 illustrates a perspective view of an aerosol delivery device according to another example implementation of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery devices or vaporization devices, said terms being used herein interchangeably. Aerosol delivery devices according to the present disclosure use electrical energy to heat a material (preferably without combusting the material to any significant degree and/or without significant chemical alteration of the material) to form an inhalable substance; and components of such devices have the form of articles that most preferably are sufficiently compact to be considered hand-held devices. That is, use of components of preferred aerosol delivery devices does not result in the production of smoke—i.e., from by-products of combustion or pyrolysis of tobacco, but rather, use of those preferred systems results in the production of vapors resulting from volatilization or vaporization of certain components incorporated therein. In preferred embodiments, components of aerosol delivery devices may be characterized as electronic cigarettes, and those electronic cigarettes most preferably incorporate tobacco and/or components derived from tobacco, and hence deliver tobacco derived components in aerosol form.

Aerosol generating devices of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), a liquid composition (e.g., commonly an aerosol precursor composition liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of the commercially available electronic aerosol delivery devices, such as those representative products referenced in the background art section of the present disclosure.

In various implementations, the present disclosure relates to aerosol delivery devices and cartridges for aerosol delivery devices that provide visual indication of one or more characteristics of the device. For example, in some implementations a cartridge of an aerosol delivery device may include a liquid composition that includes a distinctive characteristic such as, for example, a particular flavorant included in the liquid composition, or a specific strength of nicotine contained in the liquid composition, although any characteristic of the liquid composition may be considered a distinctive characteristic. The present disclosure relates to aerosol delivery devices and cartridges for aerosol delivery devices wherein, in some implementations, the cartridge is configured to be removably coupled with the control device, and wherein when the cartridge is coupled with the control device at least one feature of the cartridge, or at least one feature of the control device, or at least one feature of both the cartridge and the control device, provides a visual indication associated with the distinctive characteristic. For example, in some implementations visual indication may comprise a color associated with the distinctive characteristic. For the purposes of the current description, the term "color" should be interpreted broadly, for example covering any color or any shade of the same color. It should also be noted that in some implementations, certain colors may be commonly associated with particular distinctive characteristics; however, in other implementations, certain colors may be associated with particular distinctive characteristics according to an index or guide, which may be provided or made available to a user.

An example implementation of an aerosol delivery device 100 of the present disclosure is shown in FIG. 1. As illustrated, the aerosol delivery device 100 includes a control device 200 and a removable cartridge 300. Although only one cartridge is shown in the depicted implementation, it should be understood that, in various implementations, the aerosol delivery device 100 may comprise an interchangeable system. For example, in one or more implementations, a single control device may be usable with a plurality of different cartridges. Likewise, in one or more implementations, a single cartridge may be usable with a plurality of different control devices.

In various implementations, the control device 200 includes an outer housing 202 that defines an outer wall 204, which includes a distal end 206 and a proximal end 208. As will be discussed in more detail below, the aerosol delivery device 100 of the depicted implementation also includes an indication window 240 defined in the outer housing 202 and through which a user is provided with visual indication associated with a distinctive characteristic of the cartridge 100.

FIG. 2 illustrates a partial cross-section view of the control device 200 of the aerosol delivery device 100 of FIG. 1. As shown in the figure, the control device 200 also includes a cartridge receiving chamber 212 that is defined by an inner frame wall 214. The control device 200 further includes a battery 216 positioned within the outer housing 202 and also includes an external connection element 218. In the depicted implementation, the external connection element 218 is positioned at the distal end 206 of the outer housing 202. Electrical connectors 220 are positioned in the cartridge receiving chamber 212 and, as illustrated, are present in sides of the inner frame wall 214. It should be understood that in other implementations, the electrical connectors may be positioned in other locations of the inner frame wall 214, such as, for example the bottom of the inner frame wall 214. In another example, the electrical connectors 220 may be positioned at a point on the sides of the inner frame wall 214 between the proximal end 208 of the outer housing 202 and the bottom wall of the inner frame wall 214. Further, the electrical connectors 220 may be positioned between a midpoint of the sidewalls and the proximal end 208 of the outer housing 202 (i.e., in an upper half of the sidewalls). Alternatively, the electrical connectors 220 may be positioned between a midpoint of the sidewalls and the bottom wall of the inner frame wall 114 (i.e., in a lower half of the sidewalls). Moreover, in still other implementations, the electrical connectors may be present at any position of the inner frame wall 214. As also illustrated in FIG. 2, the proximal end 208 of the outer housing 202 includes an opening 210 that provides access to the cartridge receiving chamber 212 defined by the inner frame wall 214.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference.

In various implementations, the control device 200 may also include a light source 230 and at least one aperture 232 (see FIG. 1) defined in the outer wall 204 of the control device 200 and through which light from the light source 230 may be visible. In some implementations, the light source 230 may comprise, for example, at least one light emitting diode (LED) capable of providing one or more colors of light. In some implementations, the light source may be configured to illuminate in only one color, while in other implementations, the light source may be configured to illuminate in variety of different colors. In still other implementations, the light source may be configured to provide white light. As illustrated in FIG. 2, the light source 230 may be positioned directly on a control component 234 (such as, for example a printed circuit board (PCB)) on which further control components (e.g., a microcontroller and/or memory components) may be included. In various implementations, the aperture 232 may be provided in any desired shape and may particularly be positioned near the distal end 206 of the control device 200. In some implementations, the aperture 232 may be completely open or may be filled, such as with a light guide material, or may be covered with a transparent or translucent member (e.g., glass or plastic) on one or both of the inner surface and the outer surface of the outer wall 204 of the control device 200. The aerosol delivery device 100 may also include a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collet et al., and 2014/0270727 to Ampolini et al.; and U.S. Pub. No. 2015/0257445 to Henry et al.; which are incorporated herein by reference.

In various implementations, further indicators (e.g., a haptic feedback component, an audio feedback component, or the like) can be included in addition to or as an alternative to the light source. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. Pub. No. 2015/0020825 to Galloway et al.; and U.S. Pat. Pub. No. 2015/0216233 to Sears et al.; which are incorporated herein by reference in their entireties. It should be understood that not all of the illustrated elements are required. For example, an LED may be absent or may be replaced with a different indicator, such as a vibrating indicator.

In various implementations, an airflow sensor, pressure sensor, or the like may be included in the device. For example, as illustrated in FIG. 2, the control device 200 may include a sensor 236 on the control component 234. Configurations of a printed circuit board and a pressure sensor, for example, are described in U.S. Pat. Pub. No. 2015/0245658 to Worm et al., the disclosure of which is incorporated herein by reference in its entirety. In various implementations, the sensor 236 may be positioned anywhere within the control device 200 so as to subject to airflow and/or a pressure change that can signal a draw on the device and thus cause the battery 216 to delivery power to the heater in the cartridge 300. Alternatively, in the absence of an airflow sensor, the heater may be activated manually, such as via a push button that may be located on the control body 200 and/or the cartridge 300. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In some implementations, an input element may be included with the aerosol delivery device (and may replace or supplement an airflow or pressure sensor). The input may be included to allow a user to control functions of the device and/or for output of information to a user. Any component or combination of components may be utilized as an input for controlling the function of the device 100. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference in its entirety. As a further example, components adapted for gesture recognition based on specified movements of the aerosol delivery device may be used as an input. See U.S. Pub. 2016/0158782 to Henry et al., which is incorporated herein by reference in its entirety.

In some implementations, an input may comprise a computer or computing device, such as a smartphone or tablet. In particular, the aerosol delivery device may be wired to the computer or other device, such as via use of a USB cord or similar protocol. The aerosol delivery device may also communicate with a computer or other device acting as an input via wireless communication. See, for example, the systems and methods for controlling a device via a read request as described in U.S. Pub. No. 2016/0007561 to Ampolini et al., the disclosure of which is incorporated herein by reference in its entirety. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

Although other implementations may differ, in the depicted implementation, the cartridge receiving chamber 212 is separate from the outer housing 202. In such a manner, the cartridge receiving chamber 212 is not merely an interior space that is defined by the outer housing 202. Rather, the inner frame wall 214 defining the cartridge receiving chamber 212 may exist independently and separately from the outer housing 202. An opening of the chamber may coincide with an opening at the proximal end 208 of the outer housing 202. Thus, in the depicted implementation, the inner frame wall 214 may be a completely different element that is attached to the outer housing 202. In other implementations, however, the inner frame wall and the outer housing may be continuously formed. In either case, the sidewalls forming the inner frame wall are present interior to and separated from the outer housing.

In various implementations, the outer housing 202 may be formed of any suitable material, such as a metal, plastic, ceramic, glass, or the like. Preferably, the inner frame wall 214 is formed of the same material as used to form the outer housing 202; however, different materials may be used. Choice of materials as noted above may also extend to the outer housing for any further control device(s) that are included in the device.

An example implementation of a cartridge 300 for use in an aerosol delivery device of the present disclosure is shown in FIGS. 3 and 4. In particular, FIG. 3 is a perspective view of a cartridge according to example implementations of the present disclosure, and FIG. 4 is a partial cross-section view of the cartridge illustrated in FIG. 3. As shown in FIG. 3, the cartridge 300 includes a tank 302 that is defined by an outer tank wall 304 that includes a proximal end 306 and a distal end 308 that is closed. As such, the tank 302 may be characterized in that the tank wall 304 is a sidewall that is continuous around the tank, and the distal end 308 defines a bottom wall. The tank 302 is also configured to contain a liquid composition 324 for vaporization (e.g., an e-liquid or aerosol precursor composition), which may be configured as otherwise described herein. The cartridge 300 also includes a mouthpiece 310 that is defined by an outer mouthpiece wall 312 that includes a proximal end 314 that defines an end surface 317 with an exit portal 315 defined therein, and a distal end 316 that engages the proximal end 306 of the tank 302.

For aerosol delivery systems that are characterized as electronic cigarettes, the aerosol precursor composition may incorporate tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. Pub. No. 2015/0335070 to Sears et al., the disclosure of which is incorporated herein by reference. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

In the depicted implementation, the liquid composition, sometimes referred to as an aerosol precursor composition or a vapor precursor composition or "e-liquid", may comprise a variety of components, which may include, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol delivery system is such that the aerosol generating device provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating device. In one or more embodiments, about 1 ml or more, about 2 ml or more, about 5 ml or more, or about 10 ml or more of the aerosol precursor composition may be included.

In various implementations, the liquid composition 324 includes a distinctive characteristic. In the depicted implementation, the distinctive characteristic comprises one or more flavorants that are included in the liquid composition 324. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may in fact, represent a combination of one or more flavorants.

As shown in FIG. 4, the cartridge 300 further includes a heater 320 and a liquid transport element 322 that extends between the heater and the liquid composition 324 contained within the tank 302. In various implementations, the heater 320 and liquid transport element 322 may be configured as separate elements that are fluidly connected or may be configured as a combined element. Moreover, the heater 320 and the liquid transport element 322 may be formed of any construction as otherwise described herein. The cartridge 300 also includes one or more electrical contacts 325 that are configured to electrically connect the heater 320 with the battery 216 and/or control component 234 of the control device 200.

In various implementations, the liquid transport element 322 may be formed of one or more materials configured for transport of a liquid, such as by capillary action. In some implementations, for example, a liquid transport element may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element 322 thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. Pub. Nos. 2014/0261487 to Chapman et al. and 2014/0059780 to Davis et al.; and U.S. Pat. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element 322 may be formed partially or completely from a porous monolith, such as a porous ceramic, a porous glass, or the like. Example monolithic materials suitable for use according to embodiments of the present disclosure are described, for example, in U.S. patent application Ser. No. 14/988,109, filed Jan. 5, 2016, and US Pat. No. 2014/0123989 to LaMothe, the disclosures of which are incorporated herein by reference in their entireties. In some implementations, the porous monolith may form a substantially solid wick.

In various implementations, the heater 320 may comprise one or more different materials configured to produce heat when electrical current is applied therethrough. In some implementations, the heater 320 may be a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further implementations, the heater 320 may be formed from conductive inks, boron doped silica, and/or ceramics (e.g., positive or negative temperature coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference in its entirety. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. The heater 320 in particular may be configured to be substantially flat. Such heaters are described in U.S. Pat. Pub. No. 2016/0345633 to DePiano et al., which is incorporated herein by reference in its entirety.

In the depicted implementation, the outer tank wall 304 is configured to be at least partially transparent or translucent so that the liquid composition 324 contained therein is visible externally. As such, in some implementations, the entire outer tank wall 304 may be transparent or translucent. Alternatively, in some implementations, only a single side of the outer tank wall 304 may be transparent or translucent while the remaining portions of the outer tank wall may be substantially opaque. In some embodiments, the outer tank wall 304 may be substantially opaque, and a strip (e.g., about 1 mm wide to about 20 mm wide or about 2 mm wide to about 18 mm wide or about 5 mm wide to about 15 mm wide) extending from the proximal end 306 of the tank 302 to the distal end 308 of the tank may be transparent or translucent. In further implementations, the outer tank wall 304 may be colored. In some implementations, the color can be configured so that the liquid composition 324 within the tank 302 is still visible, such by using a transparent or translucent outer tank wall. In other implementations, the tank wall can be configured so that the outer tank wall 304 has substantially opaque color.

In various implementations, the control device 200 may be configured so that at least a portion of the tank 302 is visible when the cartridge 300 is engaged with the control device 200. As noted above, in some implementations, at least a portion of the outer tank wall 304 may be configured to be at least partially transparent or translucent so that the liquid composition 324 contained therein is visible externally, and the outer wall 204 of the control device 200 may be configured to include an indication window 240 through which a portion of the outer tank wall 304 and any liquid composition 324 present in the tank 302 can be visible when the cartridge 300 is engaged with the control device 200.

As illustrated in FIG. 1, the indication window 240 of the depicted implementation is configured as an elongated oval shaped cut-out in the outer wall 204 of the control device 200 and is located near the proximal end 208 of the control device 200; however, it should be understood that in other implementations, the indication window my have any other shape and/or location. For example, in some embodiments, the indication window 240 may be configured as a notch extending from the proximal end 208 of the outer wall 204 of the control device 200 a distance toward the distal end 206 of the device. In other embodiments, the indication window 240 may be configured so as not to have any open borders and thus may expressly exclude a notch configuration as noted above. In some implementations, the indication window 240 may be completely open, and in other implementations, the indication window may have a transparent member (e.g., glass or plastic) positioned in the opening defined by the indication window or covering the indication window on one or both of the inner surface and outer surface of the outer wall 204 of the control device 200. It should be noted that in some implementations, the indication window may be formed in part by the cartridge and in part by the control device. For example, in some implementations, the cartridge may include a portion of the indication window (e.g., a top portion of an indication window), and the control device may include a separate portion of the indication window (e.g., a bottom portion of the indication window).

In various implementations, the mouthpiece 310 of the cartridge 300 may be configured for engagement with the tank 302. For example, as illustrated in FIG. 4, the distal end 316 of the mouthpiece 310 may include a rim wall 330 that is at least partially inset from the outer mouthpiece wall 312. The rim wall 330 may be configured to engage an interior of the proximal end 306 of the outer tank wall 304. In some implementations, the rim wall 330 may have a length of about 1 mm to about 20 mm, about 2 mm to about 18 mm, or about 5 mm to about 15 mm. In some implementations, the rim wall 330 may engage the outer tank wall 304 via a friction fit alone, or the rim wall may be substantially permanently attached to the outer tank wall, such as through welding or gluing.

In some implementations, the mouthpiece 310 may define an open interior space through which formed vapor may combine with air to form an aerosol for output through the exit portal 315 of the mouthpiece 310. In one or more implementations, the mouthpiece 310 may include one or more further interior walls that can be arranged to define one or more compartments within the mouthpiece. For example, the mouthpiece may include an interior upper wall between the proximal end and the distal end of the mouthpiece and also include an interior lower wall between the interior upper wall and the proximal end of the mouthpiece. More particularly, as seen in FIG. 4, the mouthpiece 310 may include an interior upper wall 332 between the proximal end 314 and the distal end 316 of the mouthpiece 310. Further, the mouthpiece 310 may include an interior lower wall 334 between the interior upper wall 332 and the distal end 316 of the mouthpiece 310.

In various implementations, two or more walls in the mouthpiece may be configured to define a vaporization chamber within which the heater may be positioned. As shown in FIG. 4, the outer mouthpiece wall 312, the interior upper wall 332, and the interior lower wall 334 define a vaporization chamber 340 wherein the heater 320 is positioned. In some implementations, the one or more electrical contacts 325 may be positioned within the portion of the outer mouthpiece wall 312 defining the vaporization chamber 340; however, it is understood that one or more electrical leads may extend from the heater 320 to one or more electrical contacts positioned at a different portion of the outer mouthpiece wall or positioned in the outer tank wall 304. One or more walls of the mouthpiece may also include one or more openings for passage therethrough of one or more further elements of the cartridge 300 or passage of formed vapor/aerosol. For example, the interior upper wall 332 may include a vapor opening 336 through which vapor formed in the vaporization chamber 340 may pass toward the first exit portal 315. In some implementations, the vapor opening 336 in the interior upper wall 332 may be substantially centrally located therein and may be substantially aligned with the heater 320 along a longitudinal axis of the cartridge 300. As a further example, the interior lower wall 334 may include a wick aperture 338 through which the first liquid transport element 322 (e.g., a wick) can pass between the heater 320 and the liquid composition 324 in the tank 302.

In various implementations, two or more walls in the mouthpiece may be configured to define a cooling chamber within which formed aerosol can be allowed to expand and/or cool before passing through the exit portal. As shown in FIG. 4, for example, the outer mouthpiece wall 312 and the interior upper wall 332 define a cooling chamber 342 that receives formed vapor/aerosol from the vaporization chamber 340. As such, the vapor/aerosol formed by the heater 320 passes from the vaporization chamber 340 through the vapor opening 336 and into the cooling chamber 342. In some implementations, the vaporization chamber 340 and the cooling chamber 342 may be configured to have a defined relative volume ratio. For example, in some implementations, the volume ratio of the vaporization chamber 340 to the cooling chamber 342 can be about 2:1 to about 1:4, about 1:1 to about 1:4, or about 1:1.5 to about 1:3.

If desired, the mouthpiece 310 may also include one or more elements configured to reduce or prevent leakage of condensed liquids therefrom. For example, in some implementations, all or a part of the interior of the mouthpiece wall 312 and/or the interior upper wall 332 defining the cooling chamber 342 may be formed from or include an absorptive or adsorptive material configured to hold liquid. Alternatively or additionally, all or a part of the interior of the mouthpiece wall 312 and/or the interior upper wall 332 defining the cooling chamber 342 may be configured to direct liquid back toward the vaporization chamber 340, such as through the addition of microchannels or the like.

In one or more implementations, the cartridge 300 may be configured such that the mouthpiece wall 312 includes a flange positioned between the proximal end 314 and the distal end 316 thereof. For example, referring to FIGS. 3 and 4, the mouthpiece 310 includes a flange 350 that extends circumferentially from the mouthpiece wall 312 around substantially the entirety of the mouthpiece 310. In some implementations, the distance that the flange 350 extends from the mouthpiece wall 310 can be substantially uniform around the entire circumference of the mouthpiece 310. In other implementations (such as the depicted implementation) the distance that the flange 350 extends from the mouthpiece wall 312 may vary at one or more points around the circumference of the mouthpiece 310. The overall cartridge 300 or the mouthpiece 310 separately can be defined in relation to a longitudinal axis (L), a first transverse axis (T1) that is perpendicular to the longitudinal axis, and a second transverse axis (T2) that is perpendicular to the longitudinal axis and is perpendicular to the first transverse axis.

The overall cartridge 300 and/or the mouthpiece 310 thus may be defined in relation to a total length along the longitudinal axis (L), a total width along the first transverse axis (T1), and a total depth along the second longitudinal axis (T2). The length may be greater than the width, which in turn may be greater than the depth. The distance that the flange 350 extends away from the mouthpiece wall 312 may be greater along the second transverse axis (T2) than along the first transverse axis (T1). Thus, in some implementations, the total distance between opposing outer edges of the flange 350 across the mouthpiece 310 along the first transverse axis (T1) may be greater than the total distance between opposing edges of the flange across the mouthpiece along the second transverse axis (T2); the total distance between opposing outer edges of the flange 350 across the mouthpiece 310 along the first transverse axis (T1) may be substantially equal to the total distance between opposing edges of the flange across the mouthpiece along the second transverse axis (T2); or the total distance between opposing outer edges of the flange 350 across the mouthpiece 310 along the first transverse axis (T1) may be less than the total distance between opposing edges of the flange across the mouthpiece along the second transverse axis (T2). In particular implementations, a distance (d2) between the mouthpiece wall 312 and an outer edge of the flange 350 as measured along the second transverse axis (T2) may be greater than a distance between the mouthpiece wall and an outer edge of the flange as measured along the first transverse axis (T1). Said distances particularly may be as measured at about a midpoint of each of the first transverse axis (T1) and the second transverse axis (T2).

In various implementations, the electrical contacts 325, when present in the mouthpiece wall 312, may be positioned longitudinally between the flange 350 and the distal end 316 of the mouthpiece 310. Further, in some implementations, the flange 350 may be substantially in line with the interior upper wall 332. As such, the flange 350 may be substantially parallel with and/or may be substantially in the same horizontal plane with the interior upper wall 332. In some implementations, the flange 350 may be positioned above the vaporization chamber 340 and above the heater 320 along the longitudinal axis (L) of the mouthpiece 310.

In various implementations, the flange 350 may interact with a corresponding lip on the control device 200 to ensure proper connection of the cartridge 300 with the control device 200. For example, referring to FIG. 2, the control device 200 may be configured so that the opening 210 at the proximal end 208 thereof includes a recess with a first inwardly projecting lip 221. The recess thus may comprise a rim wall 222 that is substantially parallel with the longitudinal axis of the device 100. The rim wall 222 may extend downwardly from the proximal end 208 a short distance, which distance may substantially correspond to a thickness of the flange 350 of the cartridge 300 and/or the thickness of a further element that may be present adjacent the flange. For example, in some implementations, the rim wall 222 forming the downwardly extending recess may have a height (i.e., as measured from a top surface of the inwardly projecting lip 221 to the first device proximal end 208) of about 1 mm to about 8 mm, about 1 mm to about 6 mm, or about 1 mm to about 5 mm. The inwardly projecting lip 221 may have a width (i.e., the distance the lip extends inward from the rim wall 222 to a terminal end) of about 1 mm to about 8 mm, about 1 mm to about 6 mm, or about 1 mm to about 5 mm. In some implementations, the inwardly projecting lip 221 may have a substantially constant width around the entire circumference of the opening 210. In other embodiments, the inwardly extending lip 221 may be discontinuous and thus may be formed of one or a plurality of inwardly extending lips spaced around the opening 210.

In various implementations, the flange 350 of the mouthpiece 310 is configured to be at least partially received within the recess formed by the rim wall 222 so as to contact the inwardly projecting lip 221. As such, a bottom surface of the flange 350 may be substantially in contact with the inwardly projecting lip 221, and an outer edge of the flange may be substantially adjacent the rim wall 222.

In some implementations, the flange 350 and/or the inwardly projecting lip 221 may be configured to bias the cartridge 300 into connection with the control device 200. For example, a magnetic connection may be utilized. As illustrated in FIG. 4, the cartridge 300 may include a magnet 352 positioned adjacent a bottom surface of the first flange 350. In various implementations, the magnet 352 may extend substantially completely around the circumference of the mouthpiece 310 or may be discontinuous so as be configured as one or a plurality of discrete magnets. In various implementations, the magnet 352 may be adhered to the mouthpiece wall 312, may be adhered to the flange 350, or may be adhered to both the mouthpiece wall 312 and the flange 350. The inwardly projecting lip 221 may be formed of a metal or other material to which the magnet 352 will be attracted by magnetic force. In further implementations, the magnet 352 may be positioned on the control device 200. Specifically, the magnet 352 may be adhered to the inwardly extending lip 221. In such implementations, the flange 350 may be formed of a metal or other material to which the magnet 352 will be attracted by magnetic force. In further implementations, a magnet may be present on the cartridge 300 as well as the control device 200. As such, a magnet present adjacent the lower surface of the flange 350 on the cartridge 300 may be attracted by magnetic force to a magnet present adjacent the upper surface of the inwardly projecting lip 221 on the control device 200. When a magnet is present on the mouthpiece 310, it is preferable that the combined thickness of the magnet and the flange 350 is substantially identical to the height of the rim wall 222 on the control device 200 so that an upper surface of flange is substantially flush with the proximal end 208 of the device when the cartridge and the device are engaged.

In various implementations, the aerosol delivery device 100 and/or the control device 200 of the aerosol delivery device 100 may further include an external connector configured for electrical contact with each of the device external connection element (e.g., device external connection element 218). The external connector may include a first connector end and a second connector end interconnected by a union, which may be, for example, a cord of variable length. In various implementations, the first connector end may be configured for electrical and, optionally, mechanical connection with the control device. In particular, the first connector end may include an inset wall that can be received within a well present at the distal end 206 of the control device 200. The external connector may include a plurality of electrical pins interior to the inset wall configured for making a charging and/or information transferring connection with the device external connection element 218. In some implementations, the control device 200 may include a mechanical connector (e.g., a mechanical connector 242) adjacent the control device external connection element 218. In some implementations, the mechanical connector 242 may be a magnet or a metal (or like element) that is adapted for magnetic attraction to a magnet. The first connector end of the external connection may then likewise include a mechanical connection element that may be positioned between the inset wall and the electrical pins. In various implementations, the mechanical connection element may be a magnet or a metal (or like element) that is adapted for magnetic attraction to a magnet. The second connector end may be configured for connection to a computer or similar electronic device or for connection to a power source. For example, the second connector end may have a Universal Serial Bus (USB) connection; however, a different connection may also be provided and/or an adapter may likewise be included (e.g., a USB/AC adapter). For example, an adaptor including a USB connector at one end and a power unit connector at an opposing end is disclosed in U.S. Pat. Pub. No. 2014/0261495 to Novak et al., which is incorporated herein by reference.

Yet other features, controls or components that can be incorporated into aerosol delivery devices of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

In various implementations, a single control device (e.g., control device 200) may be interchangeably connectable with a plurality of cartridges (e.g., cartridge 300). Likewise, a single cartridge may be interchangeably connectable with a plurality of control devices. In various implementations of the present disclosure, the liquid composition of a particular cartridge may include a distinctive characteristic, and a color may be associated with that distinctive characteristic. In the depicted implementation, the distinctive characteristic is a flavorant. For example, in one implementation, the color green may be associated with a mint flavorant included in the liquid composition contained in a cartridge. In another implementation, the color red may be associated with an apple flavorant included in the liquid composition contained in a cartridge. In any event, the present disclosure provides that at least one indication feature of the cartridge, or at least one indication feature of the control device, or at least one indication feature of both the cartridge and the control device, produces a visual indication of the color associated with the flavorant.

In the implementation depicted in FIGS. 1-4, for example, an indication feature of the cartridge provides visual indication of the flavorant included in a liquid composition contained in the cartridge. In particular, the cartridge 300 of the depicted implementation includes an indicator band 360 (see FIG. 3) that comprises a color associated with a flavorant included in the liquid composition 324 contained in the cartridge 300. It should be noted that, in various implementations, the size, shape, and/or location of the indicator band 360 of the cartridge 300 may be configured such that when the cartridge 300 is coupled with the control device 200, at least a portion of the indicator band 360 is visible through the indication window 240 of the control device 200. In some implementations, this may be accomplished via the indicator band 360 itself; however, in the depicted implementation, the indicator band 360 further includes a projection 362 that extends upward from the indicator band 360. Although in various implementations a projection may have any configuration, in the depicted implementation, the projection 362 has a semi-circular configuration such that when the cartridge 300 of the depicted implementation is coupled with the control device 200, and when viewed through the elongated oval shaped indication window 240, the projection 362 appears as substantially circular in the bottom of the indication window 240 (as shown by example in FIG. 1). The indicator band 360 of the depicted implementation is also configured such that when the cartridge 300 is coupled with the control device 200, the level of the liquid composition contained in the cartridge 300 (e.g., as viewed through the at least partially transparent or translucent tank wall 304) is also visible through the indication window 234 and above the indicator band projection 362.

It should be noted that, in some implementations, the projection 362 may comprise a shape and/or profile that is associated with the flavorant included in the liquid composition contained in a cartridge. As such, the shape or profile of the projection 362 may be visible when the cartridge is coupled with the control device to provide visual indication of the flavorant included in the liquid composition contained in the cartridge. In various such implementations, the shapes or profiles of the projection 362 may or may not, include a color associated with the flavorant. Thus, in such implementations in which the shapes or profiles do not include a color associated with the flavorant, the shape or profile alone would provide visual indication of the flavorant included in the liquid composition contained in the cartridge.

Although in various implementations, visual indication of the color associated with the distinctive characteristic may be accomplished with an indicator of a size and shape that comprises only that portion that may be visible to a user when the cartridge is coupled with the control device, in the depicted implementation, the indicator band of the depicted implementation substantially covers the entire distal end 308 of the tank 302 and extends upward in a longitudinal axis direction (L) a distance from the distal end 308 of the tank 302 to a substantially horizontal upper edge that includes the projection 362. Such a configuration may be useful, for example, for providing clear indication of the color associated with the distinctive characteristic of the liquid composition when the cartridge is not coupled with the control device. In some implementations, this distance may comprise up to approximately 25% of the distance between the proximal end 306 and the distal end 308 of the tank 302. In other implementations, this distance may comprise between approximately 25% and 50% of the distance between the proximal end 306 and the distal end 308 of the tank 302. In other implementations, this distance may comprise approximately 50% of the distance between the proximal end 306 and the distal end 308 of the tank 302. An in still other implementations, this distance may comprise more than 50% of the distance between the proximal end 306 and the distal end 308 of the tank 302.

In another implementation of the present disclosure, the outer tank wall itself may serve as an indication feature of the cartridge that provides visual indication of a distinctive characteristic of a liquid composition contained in the cartridge. In particular, some implementations need not include an indicator band because the tank wall 304 (or a portion thereof) may comprise a color associated with a distinctive characteristic of a liquid composition contained in the cartridge 300. As such, when the cartridge 300 is coupled with the control device 200, at least a portion of the tank wall 304 comprising the color associated with the distinctive characteristic of the liquid composition may be visible through the indication window 240. In an additional implementation, the outer tank wall 304 may be at least partially transparent and/or translucent and may comprise a colored tint having the color associated with the distinctive characteristic. In such a manner, light may pass through the color tinted outer tank wall 304 and the indication window 240, thus providing visual indication of a color associated with the characteristic.

In another implementation of the present disclosure, the flange, or portion thereof, may serve as an indication feature of the cartridge that provides visual indication of a distinctive characteristic of a liquid composition contained in the cartridge. In particular, in some implementations, a portion of the flange 350 that is visible when the cartridge 300 is coupled with the control device 200 (such as, for example, at least a portion of the top surface of the flange) may comprise a color associated with a distinctive characteristic of a liquid composition contained in the cartridge 300. As such, when the cartridge 300 is coupled with the control device 200, the flange 350 provides visual indication of the color associated with the distinctive characteristic. In still other implementations, the mouthpiece, or a portion thereof, may serve as an indication feature of the cartridge that provides visual indication of a distinctive characteristic of a liquid composition contained in the cartridge. In particular, in some implementations a portion of the mouthpiece 310 (such as, for example, at least a portion of the exit portal 315 and/or at least a portion of the end surface 317) that is visible when the cartridge 300 is coupled with the control device 200 may comprise a color associated with the distinctive characteristic. For example, in the depicted implementation the exit portal 315 and a portion of the end surface 317 surrounding the exit portal 315 may comprise a color associated with a flavorant included in a liquid composition contained in the cartridge 300. As such, in various implementations, when the cartridge 300 is coupled with the control device 200, the mouthpiece 310 may provide visual indication of the color associated with a distinctive characteristic of the liquid composition.

FIG. 5 is a perspective view of a cartridge 400 according to another example implementation of the present disclosure. As shown in the figure, the cartridge 400 includes a tank 402 that is defined by an outer tank wall 404 that includes a proximal end 406 and a distal end 408 that is closed. As such, the tank 402 may be characterized in that the tank wall 404 is a sidewall that is continuous around the tank, and the distal end 408 defines a bottom wall. The tank 402 is also configured to contain a liquid composition for vaporization (e.g., an e-liquid or aerosol precursor composition), which may be configured as otherwise described herein. The cartridge 400 also includes a mouthpiece 410 that is defined by an outer mouthpiece wall 412 that includes a proximal end 414 that defines an end surface 417 with an exit portal 415 defined therein, and a distal end 416 that engages the proximal end 406 of the tank 402.

In various implementations, the cartridge 400 may have a similar configuration and may include some similar components (and similar configuration and component variations) as that of the cartridge 300 described above. As such, reference is made to the pertinent discussions of these configurations and components (and configuration and component variations). As with the implementations described above, the liquid composition contained in the tank 402 of the depicted implementation includes a distinctive characteristic, which in the depicted implementation is a flavorant. In the depicted implementation, the cartridge 400 also includes a light source 460. In some implementations, the light source 460 may comprise, for example, at least one light emitting diode (LED). In the depicted implementation, the light source 460 is configured to illuminate in the color associated with the flavorant and is located on the tank wall 404 such that it is visible through the indication window 240 of the control device 200 when the cartridge 400 is installed therein. In such a manner, when the cartridge 400 is coupled with the control device 200, the light source 460 may illuminate in the color associated with the flavorant included in the liquid composition contained in the cartridge 400. As such, when the cartridge 400 is coupled with the control device 200, the light source 460 provides visual indication of the color associated with the distinctive characteristic of the liquid composition. It should be noted that in various implementations in which a light source may be located in the cartridge (such as light source 460 of cartridge 400), the light source may be operatively connected to the power source (e.g., the battery 216) either through the same electrical contacts as are used to electrically connect the heater to the power source (such as, for example, electrical contacts similar to electrical contacts 325 of FIG. 3) or through independent contacts. Therefore, for implementations wherein the light source shares contacts with the contacts of the cartridge used to electrically connect the heater to the power source, the light source may be activated in the same manner as the heater. For implementations in which the light source includes independent contacts, the light source may be activated independently from the heater. For example, in some implementations, the light source may be activated upon coupling the cartridge with the control device. In other implementations, the light source may be activated via a user request and/or in response to a draw.

FIG. 6 is a perspective view of a cartridge 500 according to another example implementation of the present disclosure. As shown in the figure, the cartridge 500 includes a tank 502 that is defined by an outer tank wall 504 that includes a proximal end 506 and a distal end 508 that is closed. As such, the tank 502 may be characterized in that the tank wall 504 is a sidewall that is continuous around the tank, and the distal end 508 defines a bottom wall. The tank 502 is also configured to contain a liquid composition for vaporization (e.g., an e-liquid or aerosol precursor composition), which may be configured as otherwise described herein. The cartridge 500 also includes a mouthpiece 510 that is defined by an outer mouthpiece wall 512 that includes a proximal end 514 that defines an end surface 517 with an exit portal 515 defined therein, and a distal end 516 that engages the proximal end 506 of the tank 502.

In various implementations, the cartridge 500 may have a similar configuration and may include some similar components (and similar configuration and component variations) as that of the cartridge 300 described above. As such, reference is made to the pertinent discussions of these configurations and components (and configuration and component variations). As with the implementations described above, the liquid composition contained in the tank 502 of the depicted implementation includes a distinctive characteristic, which in the depicted implementation is a flavorant. In the depicted implementation, the cartridge 500 also includes a light source 560. In some implementations, the light source 560 may comprise, for example, at least one light emitting diode (LED). In the depicted implementation, the light source 560 is configured to illuminate in the color associated with the flavorant. The cartridge 500 of the depicted implementation also includes a light guide 562 that includes two ends, with a first end 564 being positioned proximate the light source 560 and a second end 566 being located on the tank wall 504, such that such that it is visible through the indication window 240 of the control device 200 when the cartridge 500 is installed therein. In such a manner, when the cartridge 500 is coupled with the control device 200, the light 560 and the light guide 562 may be configured to illuminate in the color associated with the flavorant included in the liquid composition contained in the cartridge 500. As such, when the cartridge 500 is coupled with the control device 200, the light source 560 and the light guide 562 (via light guide end 566) provide visual indication of the color associated with the flavorant included in the liquid composition. It should be noted that although in the depicted implementation the light source 560 and the light guide 562 are centrally located in the cartridge 500, in other implementations the light source 560 and/or the light guide 562 may be positioned in any position on the cartridge 500. Example structures and methods associated with directing light from a light source to a second location visible to a user are discussed in U.S. Pat. No. 8,757,147 to Terry et al., and U.S. Pat. No. 9,980,516 to Ampolini et al., each of which is incorporated by reference in its entirety.

In some implementations, the light guide may be constructed as a solid or hollow light tube made of a plastic material, such as clear or color tinted acrylic material. In other implementations, the light guide may be constructed of an optical fiber material, such as a glass optical fiber material or a plastic optical fiber material. Other implementations need not include a light guide. For example, in some implementations a light source may be disposed in the cartridge (such as, for example, proximate a distal end of the cartridge), wherein the light source may illuminate the liquid composition such that the liquid composition illuminates and/or light is visible through a sidewall of the cartridge that is tinted in a color associated with the flavorant included in the liquid composition. In another implementation, the liquid composition itself may comprise a color associated with the flavorant included in the liquid composition, and thus the illuminated liquid composition may provide visual indication of a color associated with the flavorant.

In some implementations, features of both the cartridge and the control device may provide a visual indication of a color associated with a distinctive characteristic of the liquid composition. For example, FIG. 7 illustrates partial cross-section view of a control device of an aerosol delivery device according to another implementation of the present disclosure, and FIG. 8 illustrates a cartridge configured to be received by the control device of FIG. 7. In various implementations, the control device 600 may have a similar configuration and may include some similar components (and similar configuration and component variations) as that of the control device 200 described above. As such, reference is made to the pertinent discussions of these configurations and components (and configuration and component variations). As shown therein, the control device 600 includes a cartridge receiving chamber 612 that is defined by an inner frame wall 614. The control device 600 further includes a battery 616 positioned within the outer housing 602 and also includes an external connection element 618. In the depicted implementation, the external connection element 618 is positioned at the distal end 606 of the outer housing 602. Electrical connectors 620 are positioned in the cartridge receiving chamber 612 and, as illustrated, are present in sides of the inner frame wall 614. As also illustrated in FIG. 7, the proximal end 608 of the outer housing 602 includes an opening 610 that provides access to the cartridge receiving chamber 612 defined by the inner frame wall 614. In various implementations, the control device 600 may also include a first light source 630 and at least one aperture (such as an aperture similar to aperture 232 in FIG. 1) defined in the outer wall 604 of the control device 602 and through which light from the light source 630 may be visible. In some implementations, the first light source 630 may comprise, for example, at least one light emitting diode (LED) capable of providing one or more colors of light. As also illustrated in FIG. 7, the first light source 630 may be positioned directly on a control component 634 (such as, for example a printed circuit board (PCB)) on which further control components (e.g., a microcontroller and/or memory components) may be included. However, it will be appreciated that the light source 630 may alternatively be located in any position, and thus, in some implementations, may not be located on the control component 634. As illustrated in FIG. 7, the control device 600 may also include a sensor 636 on the control component 634. The outer wall 604 of the control device 600 may also be configured to include an indication window 640 through which a portion of an outer tank wall and any liquid composition present in a tank can be visible when a cartridge is engaged with the control device 600. In the depicted implementation, the control device 600 also includes a second light source 650, which, in some implementations, may comprise, for example, at least one light emitting diode (LED) capable of providing one or more colors of light. As noted above, in some implementations, the light source may be configured to illuminate in one color. In other implementations, the light source may be configured to illuminate in variety of different colors.

As shown in FIG. 8, the cartridge 700 includes a tank 702 that is defined by an outer tank wall 704 that includes a proximal end 706 and a distal end 708 that is closed. As such, the tank 702 may be characterized in that the tank wall 704 is a sidewall that is continuous around the tank, and the distal end 708 defines a bottom wall. The tank 702 is also configured to contain a liquid composition for vaporization (e.g., an e-liquid or aerosol precursor composition), which may be configured as otherwise described herein. The cartridge 700 also includes a mouthpiece 710 that is defined by an outer mouthpiece wall 712 that includes a proximal end 714 that defines an end surface 717 with an exit portal 715 defined therein, and a distal end 716 that engages the proximal end 706 of the tank 702.

In various implementations, the cartridge 700 may have a similar configuration and may include some similar components (and similar configuration and component variations) as that of the cartridge 300 described above. As such, reference is made to the pertinent discussions of these configurations and components (and configuration and component variations). As with the implementations described above, the liquid composition contained in the tank 702 of the depicted implementation includes a distinctive characteristic, which in the depicted implementation is a flavorant. The cartridge 700 of the depicted implementation also includes a light guide 762 that defines two ends, with a first end 764 located proximate the distal end 708 of the cartridge tank 702, and a second end 766 located on the tank wall 704 such that it is visible through the indication window 640 of the control device 600 when the cartridge 700 is installed therein. In the depicted implementation, for example, when the cartridge 700 is installed in the control device 600, the first end 764 of the light guide 762 is configured to be located proximate the second light source 650 of the control device 600.

In such a manner, when the cartridge 700 is coupled with the control device 600, the light source 650 of the control device may be configured to illuminate, thus illuminating the light guide 762 such that the second end 766 of the light guide 762 displays the color associated with the flavorant included in the liquid composition contained in the cartridge 700. As such, when the cartridge 700 is coupled with the control device 600, the light source 650 and the light guide end 762 provide visual indication of the color associated with the flavorant included in the liquid composition. It should be noted that although in the depicted implementation the light source 650 and the light guide 762 are substantially centrally located in the control device 600 and cartridge 700, respectively, in other implementations the light source 650 and/or the light guide 762 may be positioned in any position within or on the control device 600 or the cartridge 700, respectively. As such, in some implementations (e.g., where the second light source 650 is also located on or proximate the control component 634), the control device 600 may also include a light guide that includes a first end located proximate the light source 650 and a second end that is located adjacent the first end 764 of the cartridge light guide 762 when the cartridge 700 is received by the control device 600. In such a manner, light from the light source 650 may be transmitted through the light guide of the control device and the light guide 762 of the cartridge in order to display the color associated with the flavorant at the second end 766 of the cartridge light guide 762. In some implementations, at least a portion of the distal end of the cartridge may be at least partially transparent and/or at least partially translucent such that light from the light source 650 may transmit through the liquid composition contained in the cartridge tank 702 without requiring a light guide 762. In such a manner, illumination of a color associated with the flavorant included in the liquid composition may be visible through the indication window 640 via the liquid composition itself.

It should be noted that in other implementations, there need not be a separate light source (such as light source 650) for providing visual indication of a color associated with the flavorant. Rather, a single light source (such as light source 630 in FIG. 7) may be used for multiple functions. Therefore, while some implementations need not include any light guides, other implementations may utilize one or more light guides to direct light from the single light source. Furthermore, in some implementations there need not be a separate aperture in the control device (such as aperture 232 in FIG. 1) such that all light based indications may occur through the cartridge, with or without the use of any light guides.

It should be noted that whereas in some of implementations above, the light source of the cartridge or the light source of the control device is configured to illuminate in the color associated with the flavorant, in other implementations, the light source of the cartridge or the light source of the control device may be configured to produce a white light, and another feature, such as, for example, a color tinted tank wall of the cartridge or a light guide, may comprise a color associated with the flavorant so that together the two features provide a visual indication of a color associated with the flavorant.

In various implementations, the light source providing the color associated with the flavorant included in the liquid composition contained in the cartridge (whether located in the cartridge or the control device) may illuminate at a variety of different times and for different periods of time. For example, in some implementations, the light source may illuminate upon coupling a cartridge with a control device and remain illuminated for a predetermined period of time. In other implementations, the light source may illuminate in response to a user request, such as, for example, by pushing a button or tapping the device. In other implementations, the light source may illuminate in response to some motion-based input, such as, for example, by waving the device in the air or by some other motion that may identified using a sensor (e.g., an accelerometer) located in the control device and/or the cartridge. In still other implementations, the light source may illuminate in response to puff detection on the device.

In some implementations, the control device may be configured to determine the flavorant included in the liquid composition contained in a coupled cartridge and illuminate a light source of the cartridge or control device (such as, for example, illuminating a light source of the cartridge or control device in the color associated with that flavorant). For example, in some implementations the control device may be able to read or sense data indicative of the flavorant included in the liquid composition from the cartridge. For example, in some implementations the control device may be configured to measure a resistance or capacitance of a cartridge wherein different resistance or capacitance values are associated with different flavorants included in the liquid composition. In various implementations, a light source of the cartridge or control device may then be controlled to illuminate in the appropriate color associated with the flavorant (or to produce white light for those implementations where another features aids in visual indication of the color). For example, in some implementations, a component of cartridge (e.g., a radio-frequency identification (RFID) chip) may be adapted to communicate with the control component of the control device by wired or wireless means. An example of an aerosol delivery system containing an RFID tag is described in U.S. Pat. App. Pub. No. 2017/0020191 to Lamb et al., which is incorporated herein by reference in its entirety. Further, various examples of control components and functions performed thereby are described in U.S. Pat. App. Pub. No. 2014/0096782 to Ampolini et al., which is incorporated herein by reference in its entirety.

As noted above, the present disclosure relates to aerosol delivery devices and cartridges for aerosol delivery devices that provide visual indication of one or more characteristics of the device wherein the visual indication is provided by at least one feature of the cartridge, or at least one feature of the control device, or at least one feature of both the cartridge and the control device. As such, although the foregoing example implementations relate to visual indication of a flavorant included in the liquid composition contained in the cartridge, other example implementations may include visual indication of other characteristics of the cartridge. For example, some implementations may provide visual indication of other features of the liquid composition contained in the cartridge (either alone or in addition to visual indication of a flavorant included in the liquid composition). For example, in some implementations, at least one feature of the cartridge, or at least one feature of the control device, or at least one feature of both the cartridge and the control device may provide visual indication of a relative strength of nicotine contained in the liquid composition.

FIG. 9 is a perspective view of a cartridge 800 according to another example implementation of the present disclosure. As shown in the figure, the cartridge 800 includes a tank 802 that is defined by an outer tank wall 804 that includes a proximal end 806 and a distal end 808 that is closed. As such, the tank 802 may be characterized in that the tank wall 804 is a sidewall that is continuous around the tank, and the distal end 808 defines a bottom wall. The tank 802 is also configured to contain a liquid composition for vaporization (e.g., an e-liquid or aerosol precursor composition), which may be configured as otherwise described herein. The cartridge 800 also includes a mouthpiece 810 that is defined by an outer mouthpiece wall 812 that includes a proximal end 814 that defines an end surface 817 with an exit portal 815 defined therein, and a distal end 816 that engages the proximal end 806 of the tank 802.

In various implementations, the cartridge 800 may have a similar configuration and may include some similar components (and similar configuration and component variations) as that of the cartridge 300 described above. As such, reference is made to the pertinent discussions of these configurations and components (and configuration and component variations). In the depicted implementation, the liquid composition contained in the tank 802 includes a distinctive characteristic, which in the depicted implementation is a nicotine component of a specific strength. In various implementations, a portion of the mouthpiece wall 812 may comprise a color, or a shade of a color, associated with the relative strength of the nicotine component. For example, in some implementations, three different versions of the cartridge 800 may contain liquid compositions comprising three different nicotine strengths, such as, for example, a low strength, a medium strength, and a high strength. As such, a color or a shade of a color of the mouthpiece wall 812 may be associated with each different nicotine strength, such as, for example, a light shade of gray for the mouthpiece wall 812 associated with the low nicotine strength liquid composition, a medium shade of gray for the mouthpiece wall 812 associated with the medium nicotine strength liquid composition, and a dark shade of gray for the mouthpiece wall associated with a high nicotine strength liquid composition. It should be noted that in other implementations, the characteristic of the cartridge may differ and other features of the cartridge, the control device, or both the cartridge and control device, as similarly described above, may serve to provide visual indication of the characteristic. Thus, as noted above the examples provided herein should not operate to limit the present disclosure.

It should be noted that although the examples described and illustrated herein depict aerosol delivery devices having a removable cartridge with a "pod-mod" design, the present disclosure is equally applicable to any other form of an aerosol delivery device, including, for example, devices having sizes and shapes configured to resemble traditional cigarettes, such as those similar to the device described in U.S. Pat. No. 8,499,766 to Newton, as well as devices that may or may not, include a tank, such as, for example, devices similar to the various VUSE® products produced by R. J. Reynolds Vapor Company, such as devices similar to the Ciro®, Vibe™, and Solo® devices. Thus, for example, aspects of the disclosure may be applied mutatis mutandis to indicate a distinctive characteristic of a liquid contained in a cartridge of aerosol delivery devices in which the cartridge is coupled with a control body in an aligned end to end arrangement (e.g., via a threaded, snap-fit, and/or magnetic connection).

For example, FIG. 10 illustrates a perspective view of an aerosol delivery device according to another example implementation of the present disclosure. In particular, FIG. 10 depicts an aerosol delivery device 1000 that includes a control device 1200 and a removable cartridge 1300. In various implementations, the cartridge 1300 is configured to be coupled with the control device 1200 via a threaded, snap-fit, magnetic, and/or other similar connection. In the depicted implementation, the cartridge 1300 includes a tank 1302 that is defined by an outer tank wall 1304. The cartridge 1300 of the depicted implementation also includes an atomizer unit 1350, which is located on a distal end thereof. In some implementations, the atomizer unit 1350 maybe separable from the cartridge 1300. The tank 1302 of the depicted configuration is configured to contain a liquid composition for vaporization (e.g., an e-liquid or aerosol precursor composition), which may be configured as otherwise described herein. For example, in the depicted implementation, the liquid composition includes a distinctive characteristic. In many aspects, the cartridge 1300 and the control device 1200 may have similar configurations and may include some similar components (and some similar configuration and component variations) as the cartridges and control devices described above. As such, reference is made to the pertinent discussions of these configurations and components (and configuration and component variations In the depicted implementation, the aerosol delivery device 1000 includes a light source 1360. Although in various implementations the location of a light source may vary (e.g., in some implementations, the light source 1360 maybe located on, or inside of, the cartridge 1300 (including on, or inside of, the atomizer 1350), and/or the control device 1200), in the depicted implementations, the light source 1360 is located inside the tank 1302. In some implementations, the light source 1360 may comprise, for example, at least one light emitting diode (LED). In the depicted implementation, the light source 1360 is configured to illuminate in a color associated with the distinctive characteristic of the liquid composition. In such a manner, when the cartridge 1300 is coupled with the control device 1200, visual indication of the color associated with the distinctive characteristic may be provided to a user. In other implementations, the outer tank wall 1304 maybe at least partially transparent and/or translucent and may comprise a colored tint having the color associated with the distinctive characteristic. In such a manner, light may pass through the color tinted outer tank wall, thus providing visual indication of the color associated with the distinctive characteristic. It should be noted that in other implementations, one or more light guides may facilitate the visibility of the light source. In such a manner, when the cartridge 1300 is coupled with the control device 1200, one or more light guides may facilitate providing visual indication of the color associated with the distinctive characteristic.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:
a cartridge that comprises a mouthpiece and that includes an aerosol precursor composition, the aerosol precursor composition including a distinctive characteristic; and
an outer body having an end configured to couple with the cartridge so that a portion of the cartridge including the aerosol precursor composition is arranged inside the outer body and the mouthpiece extends out from the outer body,
wherein when the cartridge is coupled with the outer body, at least one feature of the aerosol delivery device provides a visual indication associated with the distinctive characteristic.

2. The aerosol delivery device of claim 1, wherein the distinctive characteristic comprises a flavorant included in the aerosol precursor composition.

3. The aerosol delivery device of claim 1, wherein the visual indication comprises a color associated with the distinctive characteristic.

4. The aerosol delivery device of claim 1, wherein the outer body includes at least one light source therein, and wherein the light source at least partially provides the visual indication associated with the distinctive characteristic.

5. The aerosol delivery device of claim 3, wherein the cartridge has an exit portal defined through a portion thereof, and wherein the exit portal provides the visual indication of the color associated with the distinctive characteristic.

6. The aerosol delivery device of claim 5, wherein the exit portal has an oblong shape.

7. The aerosol delivery device of claim 1, wherein the aerosol precursor composition comprises a liquid composition.

8. The aerosol delivery device of claim 1, wherein at least a portion of the cartridge is transparent.

9. The aerosol delivery device of claim 1, wherein the mouthpiece is integrated with the cartridge.

10. The aerosol delivery device of claim 1, wherein the outer body includes an external connection element configured for charging the aerosol delivery device.

11. The aerosol delivery device of claim 1 further comprising a control mechanism configured to control an amount of electrical power delivered to the aerosol delivery device.

12. The aerosol delivery of claim 1 further comprising an end cap configured to engage at least a portion of a distal end of the outer body.

13. The aerosol delivery device of claim 1, wherein the outer body includes a power source.

14. The aerosol delivery device of claim 13, wherein the power source comprises a battery configured to be removable from the outer body.

15. The aerosol delivery device of claim 1, wherein the cartridge comprises a reservoir that holds the aerosol precursor composition.

* * * * *

UNITED STATES PATENT AND TRADEMARK OFFICE
CERTIFICATE OF CORRECTION

PATENT NO. : 12,239,164 B2
APPLICATION NO. : 18/618302
DATED : March 4, 2025
INVENTOR(S) : Jared Aller et al.

It is certified that error appears in the above-identified patent and that said Letters Patent is hereby corrected as shown below:

In the Claims

In Column 28, Line 22, in Claim 12, after "delivery" insert -- device --.

Signed and Sealed this
Eighth Day of July, 2025

Coke Morgan Stewart
*Acting Director of the United States Patent and Trademark Office*